United States Patent [19]
Davis et al.

[11] Patent Number: 5,196,019
[45] Date of Patent: Mar. 23, 1993

[54] GONIOMETER FOR NEEDLE PLACEMENT

[75] Inventors: Richard E. Davis, Grand Rapids, Mich.; John E. Drace, Portola Valley, Calif.

[73] Assignee: DLP, Inc., Grand Rapids, Mich.

[21] Appl. No.: 771,627

[22] Filed: Oct. 4, 1991

[51] Int. Cl.$^5$ ............................................. A61B 19/00
[52] U.S. Cl. ........................................ 606/130; 378/81; 604/264
[58] Field of Search ............... 606/130, 167; 604/264; 378/81; 248/542, 543

[56] References Cited

U.S. PATENT DOCUMENTS

| | | | |
|---|---|---|---|
| 3,115,140 | 12/1963 | Volkman | 606/130 X |
| 3,839,635 | 10/1974 | Chan et al. | 378/81 |
| 4,058,114 | 11/1977 | Soldner | 606/130 X |
| 4,230,117 | 10/1980 | Anichkov | 606/130 |
| 4,534,050 | 8/1985 | Smith | 606/130 X |
| 4,608,977 | 9/1986 | Brown | 606/130 |
| 4,846,173 | 7/1989 | Davidson | 606/130 |
| 5,004,457 | 4/1991 | Wyatt et al. | 606/130 X |
| 5,030,223 | 7/1991 | Anderson et al. | 606/130 |
| 5,053,042 | 10/1991 | Bidwell | 606/130 |

Primary Examiner—Peter A. Aschenbrenner
Attorney, Agent, or Firm—Barnes, Kisselle, Raisch, Choate, Whittemore & Hulbert

[57] ABSTRACT

A goniometer for needle placement in connection with a computer tomograph to direct a needle at a proper angle to reach an area for biopsy or other surgical procedures in the human body. One embodiment of the device includes a double ring, the outer ring having arcuate graduations and a level mounted thereon, and the inner ring being rotatable in the outer ring to various angle positions and including a needle carrier for receiving a needle holder.

The outer ring has serrations on a continuous arcuate surface and the inner ring has resilient detents to contact and rid on the serrations. A lever operated needle holder has a cam to lock a detent into a serration when the needle holder is moved to a position to retain a needle.

11 Claims, 3 Drawing Sheets

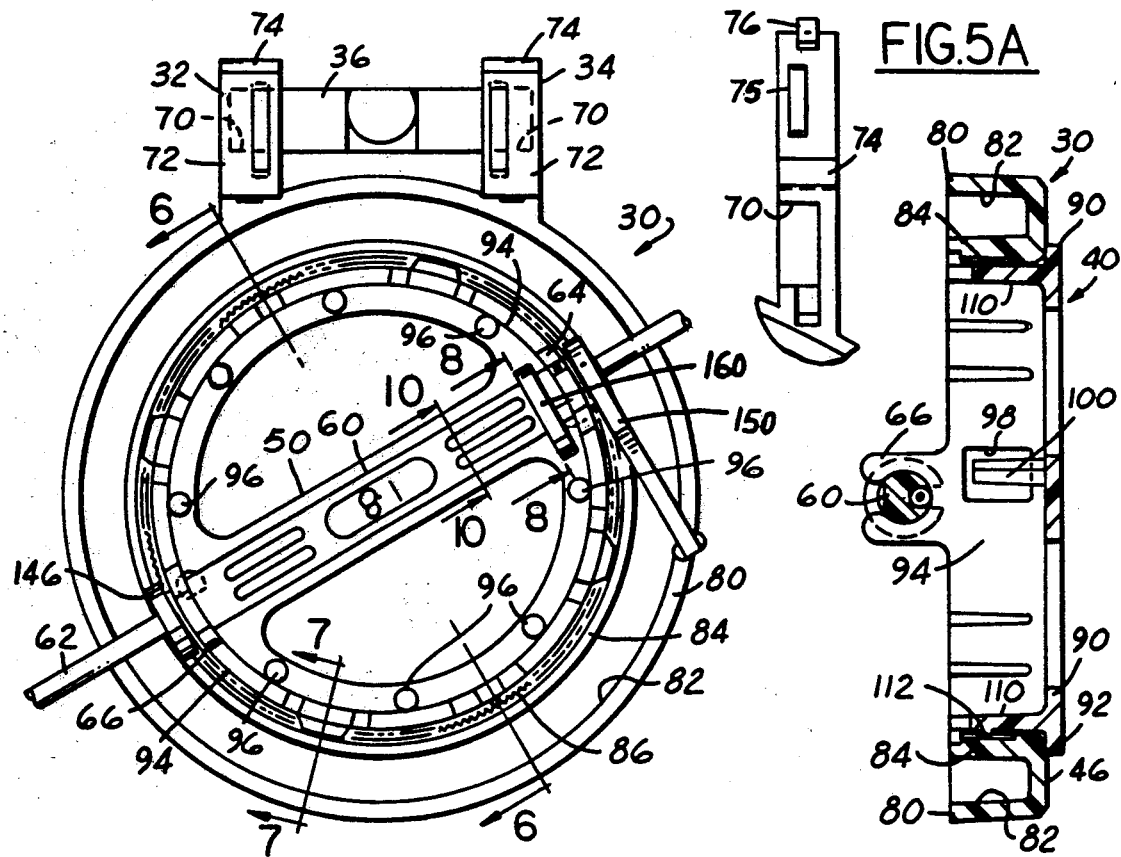

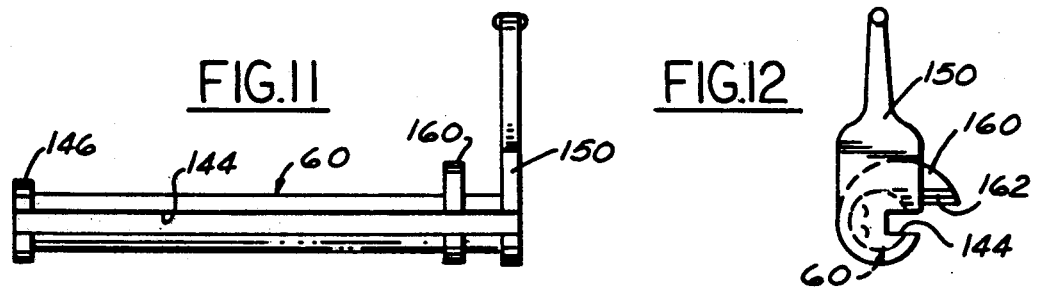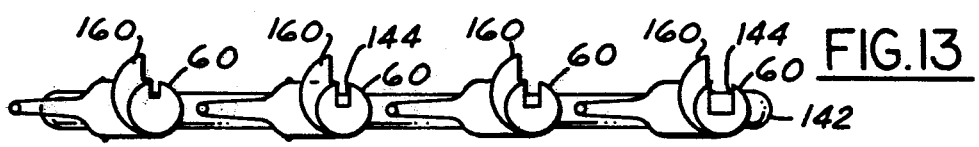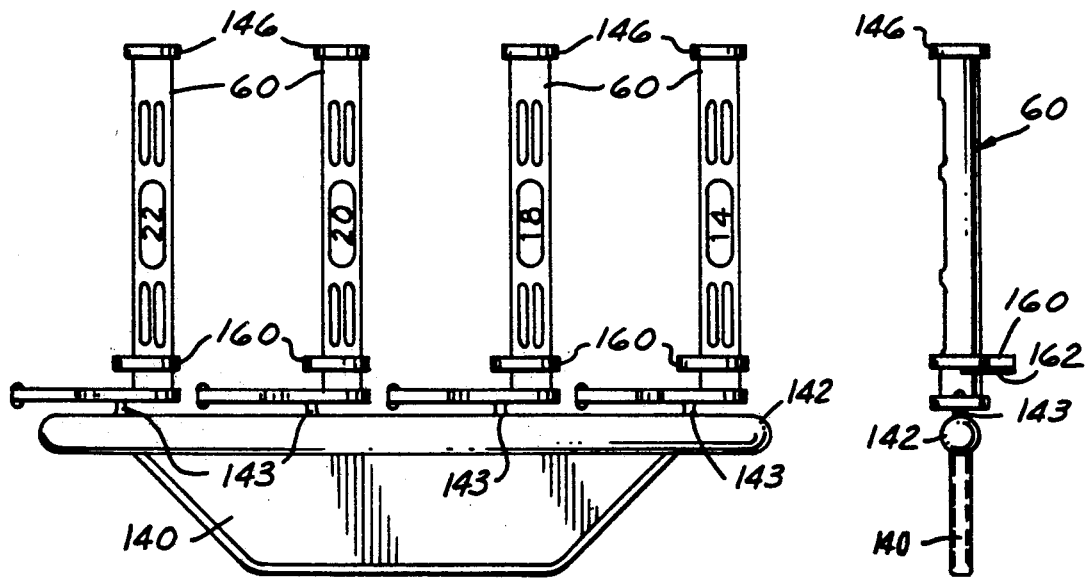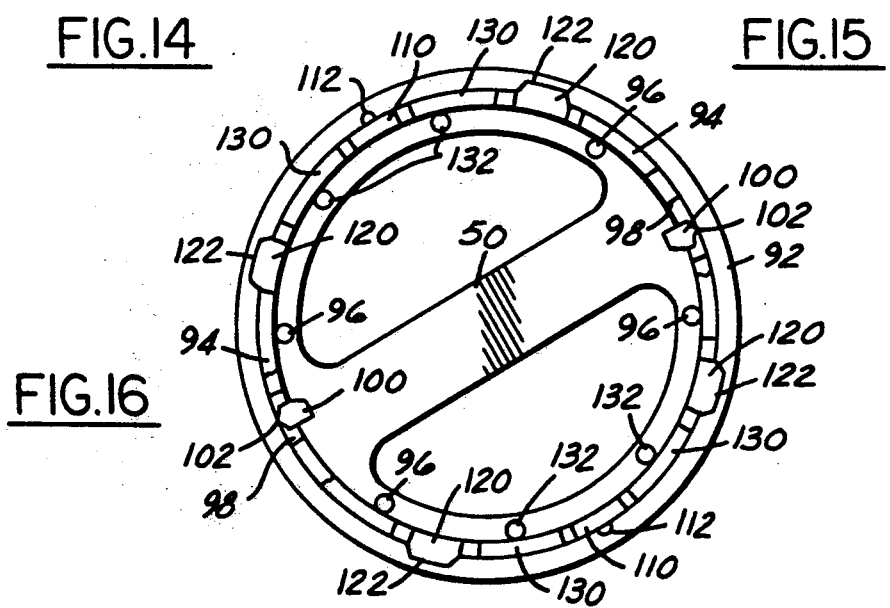

GONIOMETER FOR NEEDLE PLACEMENT

FIELD OF INVENTION

A hand held guide for mounting a needle, catheter and the like and placing the guide on a portion of the human body, usually an abdominal area, with an angle disposition to direct the needle to a specific area and place in conjunction with a computer tomographic (CT) X-ray scanner.

BACKGROUND AND FEATURES OF THE INVENTION

With advanced X-ray technology, it is possible to locate, within the human body, tumors, growths, or areas which should be explored by biopsy techniques or excised by surgical procedures. Existing patents are directed to hand held devices which enable a physician to direct a needle or catheter into the patient with accurate placement. A Soldner U.S. Pat. No. 4,058,114, disclosing an ultrasonic arrangement for puncturing internal organs, issued Nov. 15, 1977. In April of 1986, a patent issued to Onik, U.S. Pat. No. 4,583,538 on a method and apparatus for stereotactic placement using CT scanners. Also in June 1986 a U.S. Pat. No. 4,592,352 issued to Patil on a computer assisted tomography stereotactic system. A Plaestrant U.S. Pat. No. 4,733,661, issued Mar. 29, 1988 on a Guidance Device for C.T. Guided Drainage and Biopsy Procedures.

The present invention is directed to a stereotactic goniometer which will assist in accurate needle placement during computer tomographic (CT) guided biopsies, aspirations and similar techniques. It is an object to provide a small and easily handled device which is more convenient, faster, and more accurate than previous devices and which is relatively economical and very light so that it may be left attached during respiration.

The present invention comprises an adjustable needle carrier with angle indications mounted in a frame having a compass orientation fixture. Needle mounts are included on the carrier with a kit attachment for accepting needles of varying dimensions to be mounted selectively on the needle carrier. Locking devices are provided on the needle mounts to enclose a selected needle in the needle carrier. A detent lock is also provided to establish a particular angle for a needle position. Thus, the assembly includes an angle adjustable mount, a leveling device, a kit with varying size needle mounts to position and be locked on the carrier, and a detent lock to locate the needle in a selected position.

Other objects and features in addition to those enumerated will be apparent in the following description and claims in which details of the invention are set forth to enable persons in the art to practice the invention, all in connection with the best mode presently contemplated for the invention.

BRIEF DESCRIPTION OF THE DRAWINGS

DRAWINGS accompany the disclosure and the various views thereof may be briefly described as:

FIG. 5, an enlarged rear face view of the needle holder taken on line 5—5 of FIG. 4.

FIG. 5A, a view of a level retainer prior to enclosure.

FIG. 6, a sectional view on line 6—6 of FIG. 5.

FIG. 7, a sectional view on line 7—7 of FIG. 5.

FIG. 8, a sectional view on line 8—8 of FIG. 5.

FIG. 8A, a view similar to FIG. 8 with parts moved to an open position.

FIG. 9, a small section on line 9—9 of FIG. 8. of FIG. 5.

FIG. 10, a small section on line 10—10

FIG. 11, an elevation of a needle holder.

FIG. 12, an end view of the needle holder.

FIG. 13, a side view of a needle kit.

FIG. 14, an elevation of the needle kit.

FIG. 15, an end view of the needle kit.

FIG. 16, a back view of the needle retainer prior to assembly.

DETAILED DESCRIPTION OF THE INVENTION

The Two-Piece Rotary Goniometer

Figure 1:
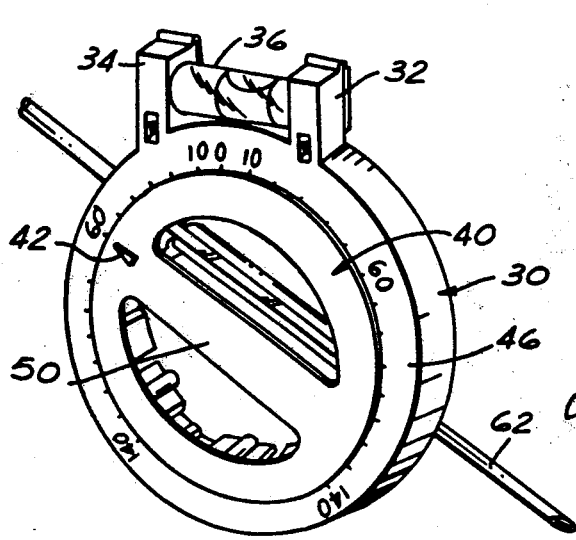
FIG. 1, a perspective view of the front of the needle holder.

With reference to the drawings, in FIG. 1, a perspective view of the front face of the assembled goniometer is illustrated showing a circular main outer housing race 30 which carries spaced level supports 32,34 at the top in which a bubble level tube 36 is mounted. Within the outer race 30 is a rotatable needle carrier ring 40 which has an arrow 42 to relate to degree markings on a front face 46 of the outer race. The needle carrier ring 40 has a diametrical cross bar 50 which serves as a finger hold to rotate the carrier in the outer ring 30.

Figure 2:
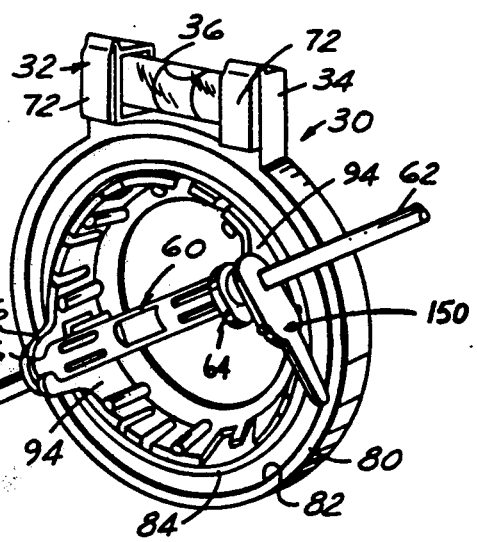
FIG. 2, a perspective view of the rear side of the needle holder.
Figure 3:
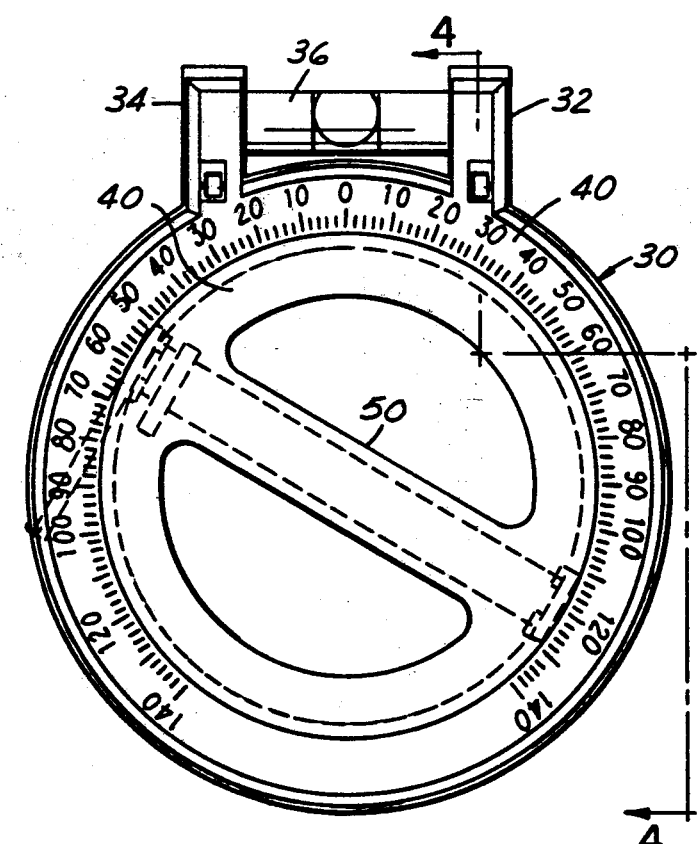
FIG. 3, an enlarged front elevation of the assembly.
Figure 4:
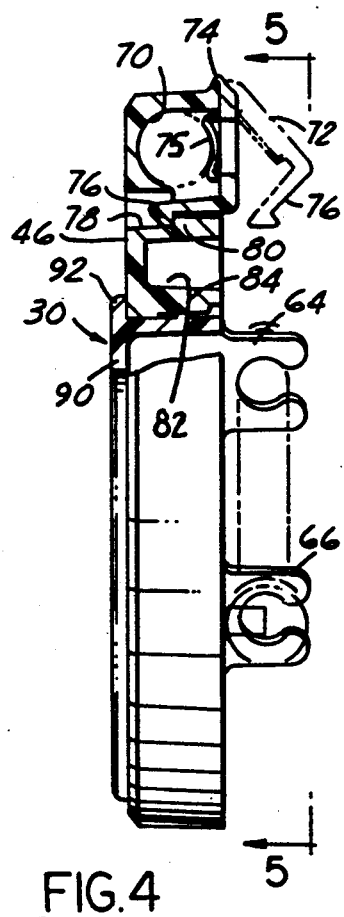
FIG. 4, a partial section on line 4—4 of FIG. 3.

FIG. 2 is a perspective view of the rear side of the assembly showing a removable needle holder 60 carrying a needle 2 and additional details of the carrier to be described. FIG. 3 illustrates a face-on view of the assembly and FIG. 4 is a side view, partially in section, taken on line 4—4 of FIG. 3. In FIGS. 2 and 4 are shown rearwardly extending, diametrically spaced, snap-in retainers 64,66 which are designed to mount needle holders 60 on the rotatable needle carrier 40

The level supports 32,34 each have a recess 70, as shown in FIGS. 4, 5 and 5A, to receive and retain the ends of the level tube 36. Molded with each support is a snap-in closure face plate 72 which is attached to the support by a living hinge 4. Each plate has an inside ridge 75 to contact the end of a level tube. Each face plate 72 has an integral projection 76 with a locking detent which enters and snaps in to a recess 78 in the outer race 30 as best shown in the sectioned portion of FIG. 4.

The outer race 30 of the goniometer consists of a double ring which has an outside circular wall 80 best shown in FIGS. 2 and 6 inside of which is an annular groove 82, the inside base of which is the annular face 46 with the angle graduations 0° to 140° extending in each direction from the 0°. Concentric with the outer wall 80 and the 9roove 82 is an inner wall 84. On the inside surface of the inner wall 84 are fine serrations 86 extendin9 axially around the wall 84, as seen in FIG. 5.

The circular needle carrier 40, which rotates within the outer ring 30, has a front face 90 with a narrow flange extension 92 which overlies the inner edge of the graduated face 46 on the outer race housing. This carrier has also the diametrical cross bar 50. Behind the front face wall 90 and inside the flange extension 92 are axially extending arcuate walls 94 disposed at each end of the bar 50. The snap-in needle retainers 64,66, FIGS. 2 and 6, extend from these walls 94. Two axially extending reinforcement posts 96 are molded with the walls 94. Between the ends of the walls 94 is a small window 98 behind which is a detent prong 100 having a small ridge or tooth 102 extending through this window. This ridge is positioned to engage the serrations 86 on the inside surface of the inner wall 84 of the outer race 30. The prong 100 is resilient so that it will flex inwardly as the inner needle carrier is rotated around the serrations. Additional detent prongs 110 (FIGS. 6 and 11) with small projections 112 are spaced circumferentially between the prongs 100 to contact also the serrations 86 to provide rotation resistance.

The inner rotary needle carrier 40 is retained in the main outer race by latch projections 120 which extend also axially from the ring 90 of the rotary part 40. These projections 120 have small latch tabs 122 (FIGS. 7 and 16) which snap over the inner rim 84 of the outer race 30 to lock the inner rotor 40 axially into the outer race 30. Additional short projections walls 130 are interspaced between the projections 94 and 120 also reinforced by posts 132.

The Needle Holder Kit

The snap-in retainers 64,66 above described are provided to mount and retain needle holders 60 shown in the assembly in FIGS. 2, 5 and 6. In FIG. 14, a molded plate 140 has an integral rod 142 to which are attached, by frangible connectors 143, four needle holders 60 with numerical size indicia 14,18,20 and 22 designating four different needle size grooves 144.

In FIGS. 11 and 12, the details of the needle holders 60 are illustrated. Each holder comprises an elongate shaft with the slot or groove 144 extending the full length. At the left-hand end as viewed in FIG. 11 is a flange 146 which, when mounted on the goniometer assembly, lies adjacent and outside a snap-in retainer 66 as shown in FIG. 5. At the right-hand end of the needle holder 60 as viewed in FIGS. 11 and 12 are two functional elements molded integrally with the holder. At the extreme end is a lever 150 notched at one side in alignment with slot 144. This lever facilitates rotation of the holder 60 when a needle is loaded in the slot 144. Spaced inside the lever 150 is a cam-like curved piece 160 also notched at the slot 144. This cam piece 160 has a ridge 162 (FIGS. 12 and 15) which functions to lock the inner rotor as will be described.

When the needle holder 60 is disposed within the carrier 40 between the snap-in retainers 64,66 as shown in FIG. 2, it can be rotated by the lever 150 to a position shown in FIG. 8A with the slot groove 144 open to receive a needle. Once a needle is placed in the groove 144, the lever 150 can be rotated to the position shown in FIGS. 5 and 8. This closes the needle slot to enclose the needle. Also, the cam piece 160 is rotated toward the position shown in FIG. 8. Assuming that the rotary needle carrier is moved to an angle position for needle injection, full movement of the lever 150 also moves the cam piece 160 to a position where the ridge 162 cams the prong 100 outwardly to lock the tooth 102 in a serration 86 on the inner wall of the ring 30. This position is shown in FIG. 9. With this locked position the rotatable needle carrier cannot be accidentally shifted after the initial angle setting by the surgeon.

Use of the Goniometer Assembly

The following steps can be followed in the use of the above-described kit:

1. Remove the goniometer ring assembly and the multiple needle holder assembly (FIG. 14) from a sterile package.
2. Select axial/slide needed for the biopsy or drainage procedure. Place a radiopaque marker on the skin and rescan with the computer tomography.
3. Select the needle entry point.
4. Draw a line representing the needle path on the monitor using the appropriate computer tomography console
5. Mark the entry point on the skin.
6. Prepare the skin in the customary sterile method.
7. With one hand, grasp the outer ring of the goniometer and with the other hand, grasp the inner ring crossbar and turn to the selected angle.
8. After selecting the biopsy needle gauge, break the appropriate size needle guide from the four selections.
9. Insert the needle guide into the snap-in retainers 64,66 with the needle slot visible (FIG. 8A).
10. Insert the needle throughout the guide holder opening with the needle in the needle slot.
11. Rotate the needle guide holder to enclose the needle (FIG. 5) and lock the inner ring in the outer ring.
12. Retract the needle end to a position behind the outer ring 30.
13. Place the goniometer ring against the skin and orient it in the bubble in the level tube 36.
14. Advance the needle to the mark on the patient's skin. Puncture the skin and advance the needle to the targeted
15. The needle gauge can be rotated to expose the needle slot 144 (FIG. 8A) and thus the needle guide may be removed from the needle.
16. Scan to confirm the needle position and proceed with the planned function.

What is claimed is:
1. A goniometer comprising:
   (a) a first support member in the form of an outer ring having an outer diameter and an inner diameter,
   (b) a bubble level on said first support member to orient the first support member relative to a horizontal position,
   (c) a second support member in the form of an inner ring to rotate within said outer ring,
   (d) a needle carrier on said second support member to receive needles selectively of varying sizes,
   (e) means associating said support members for relative rotation, said means comprising a first surface on one of said members, and means on the other of said members operatively associated with said first surface to control said relative rotation,
   (f) a graduated surface on one of said support members to provide visual observation of the relative adjusted rotation of said one support member relative to the other support member, and
   (g) said means associating said support members comprising serrations formed on said first surface of said outer ring, and means on the other of said members comprise a resilient detent formed on said inner ring to contact and ride over said serrations to a selected position of rotation of said inner ring.
2. A goniometer comprising:
   (a) a first support member in the form of an outer ring having an outer diameter and an inner diameter,

(b) a bubble level on said first support member to orient the first support member relative to a horizontal position, (c) a second support member in the form of an inner ring to rotate within said outer ring, (d) a needle carrier on said second support member to receive needles selectively of varying sizes, (e) means associating said support members for relative rotation, said means comprising a first surface on one of said members, and means on the other of said members operatively associated with said first surface to control said relative rotation, (f) a graduated surface on one of said support members to provide visual observation of the relative adjusted rotation of said one support member relative to the other support member, and (g) releasable mounting means positioned diametrically on said inner ring, and a needle holder designed to fit into said mounting means to hold a needle.

3. A goniometer comprising:

(a) a first support member in the form of an outer ring having an outer diameter and an inner diameter, (b) a bubble level on said first support member to orient the first support member relative to a horizontal position, (c) a second support member in the form of an inner ring to rotate within said outer ring, (d) a needle carrier on said second support member to receive needles selectively of varying sizes, (e) means associating said support members for relative rotation, said means comprising a first surface on one of said members, and means on the other of said members operatively associated with said first surface to control said relative rotation, (f) a graduated surface on one of said support members to provide visual observation of the relative adjusted rotation of said one support member relative to the other support member, and (g) said orienting level comprising a closed bubble tube mounted parallel to a diameter of said outer ring and in which spaced level supports extend outwardly from the outer ring, facing recesses on said supports to receive the ends of said bubble tube, entrance openings on said supports leading to said recesses, and closure plates hinged on said supports movable to a closed position to close said entrance openings and lock the ends of said tube in said recesses.

4. A goniometer as defined in claim 3 in which said closure plates are connected to said supports by a living hinge molded with said supports and a locking projection extending normal to said closure plates at the free end, each having a locking detent to snap into a recess in said respective supports.

5. A goniometer as defined in claim 1 in which said serrations are formed on the inside diameter of said outer ring, and said inner ring has a back surface with projections extending normal to the plane of said ring, a first of said projections comprising said resilient detent having a tooth to engage said serrations as said inner ring is rotated in said outer ring.

6. A goniometer as defined in claim 5 in which one or more second axial projections on said inner ring contact said serrations to provide resistance to rotation.

7. A goniometer as defined in claim 6 in which a plurality of third axial projections project axially past the inner diameter of said outer ring, and tabs on said third projections latch over the inner diameter of said outer ring to lock the inner and outer rings axially together.

8. A goniometer as defined in claim 2 in which said needle holder comprises an elongate shaft having a side slot to receive a needle, means on each end of said shaft to be releasably received on said inner ring to position said holder diametrically of said inner ring spaced from the plane of said rings, a lever extending from one end of said shaft to enable rotation of said shaft from a position in which said slot is exposed to receive a needle to a position in which said slot is occluded in a locking position to retain a needle, cam means on said needle shaft movable upon rotation of said shaft to a position to move a projection into a locking position against serrations on said outer ring.

9. A goniometer comprising:

(a) a first support member in the form of an outer ring having an outer diameter and an inner diameter, (b) a bubble level on said first support member to orient the first support member relative to a horizontal position, (c) a second support member in the form of an inner ring to rotate within said outer ring, (d) a needle carrier on said second support member to receive needles selectively of varying sizes, (e) means associating said support members for relative rotation, said means comprising a first surface on one of said members, and means on the other of said members operatively associated with said first surface to control said relative rotation, (f) a graduated surface on one of said support members to provide visual observation of the relative adjusted rotation of said one support member relative to the other support member, (g) serations formed on an arcuate surface on said outer ring, (h) a flexible resilient detent formed on said inner ring to contact and ride over said serrations to a selected position of rotation of said inner ring, (i) said needle holder comprising an elongate shaft having a side slot to receive a needle, (j) means on each end of said shaft to be releasably received on said inner ring spaced from the plane of said rings, (k) a lever extending from one end of said shaft to enable rotation of said shaft from a position in which said slot is exposed to receive a needle to a position in which said slot is occluded in a locking position to retain a needle, (l) cam means on said needle shaft movable upon rotation of said shaft to a locking position, (m) a cam projection on said cam means to move said resilient detent into firm contact with said serrations to lock said inner ring against movement in said outer ring.

10. A goniometer to be hand held in relation to a patient to direct a needle into a patient for a biopsy or other surgical procedures, comprising an assembly of two rings to be positioned in a vertical plane above the area of a patient to be treated, the assembly comprising:

(a) a first support member in the form of an outer ring having an outer diameter and an inner diameter, (b) a bubble level in the form of a container mounted on said first support member lying in the plane of said outer ring to orient the hand held assembly relative to horizontal position, (c) a second support member in the form of an inner ring lying in the same plane as the outer ring and mounted to rotate to fixed positions within the outer ring, and (d) a needle holder mounted on and extending diametrically across said second support member to receive needles of varying sizes.

11. A goniometer as defined in claim 9 in which said outer ring is graduated by degrees from a 0° point to 140° in each circumferential direction, said bubble level being mounted at the zero point parallel to a diameter intercepting the diametrically spaced 90° graduations.

* * * * *